United States Patent [19]

Losi

[11] Patent Number: 5,011,404

[45] Date of Patent: Apr. 30, 1991

[54] APPLIANCE FOR CORRECTING DENTAL MALPOSITIONS

[75] Inventor: Enrico Losi, Milan, Italy

[73] Assignee: Franca Losi, Cinisello Balsamo, Italy; a part interest

[21] Appl. No.: 357,937

[22] Filed: May 26, 1989

[30] Foreign Application Priority Data

May 26, 1988 [JP] Japan .................................. 63-20751

[51] Int. Cl.$^5$ ............................................... A61C 3/00
[52] U.S. Cl. .......................................... 433/19; 433/21
[58] Field of Search ....................... 433/18, 19, 20, 21

[56] References Cited

U.S. PATENT DOCUMENTS 2,580,042 12/1951 Paus ....................................... 433/21

FOREIGN PATENT DOCUMENTS 335395 2/1936 Italy ...................................... 433/19
1012893 12/1965 United Kingdom .................... 433/20

Primary Examiner—Cary E. Stone
Attorney, Agent, or Firm—Browdy and Neimark

[57] ABSTRACT

An appliance is disclosed for the correction of dental malpositions, and particularly for the distalization of molar teeth. A metal wire arch is fastened to the incisors and canines, and at least one small tube receives a portion of the wire arch which can move freely inside the tube. The tube has a fixed protrusion which is in contact with a coil-spring wound around the tube at one end. The coil-spring engages a sleeve fastened onto a metal band which is fitted to a malpositioned molar tooth. At the other end, the tube is provided with a hook-shaped projection. An inter-maxillary rubber band engages the hook and a similar hook-projection fastened to a molar of the antagonist jaw. The appliance is of the intra-oral and non-movable type, which is used to carry out a functional treatment which is similar to biological and natural rhythms. This device uses the muscular force that the patient exerts in order to tense the inter-maxillary elastic, when talking or chewing.

16 Claims, 3 Drawing Sheets

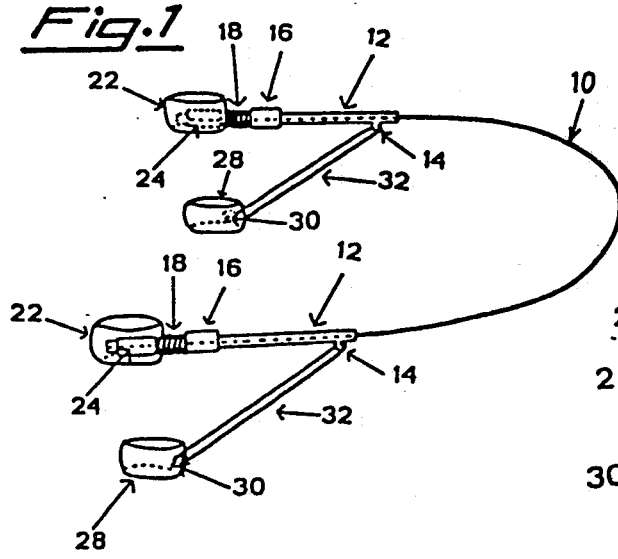
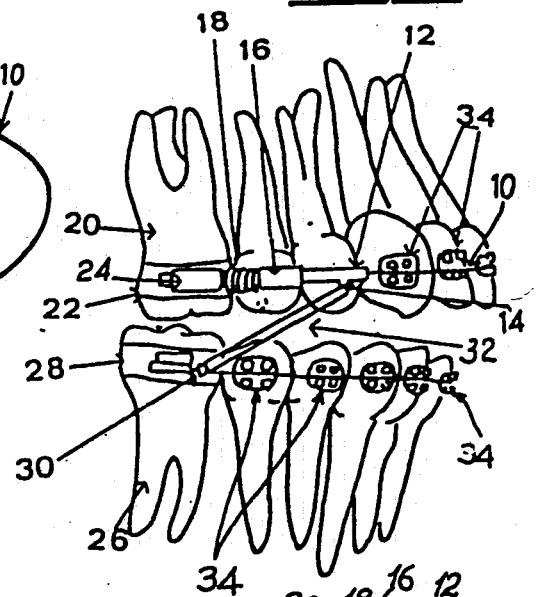
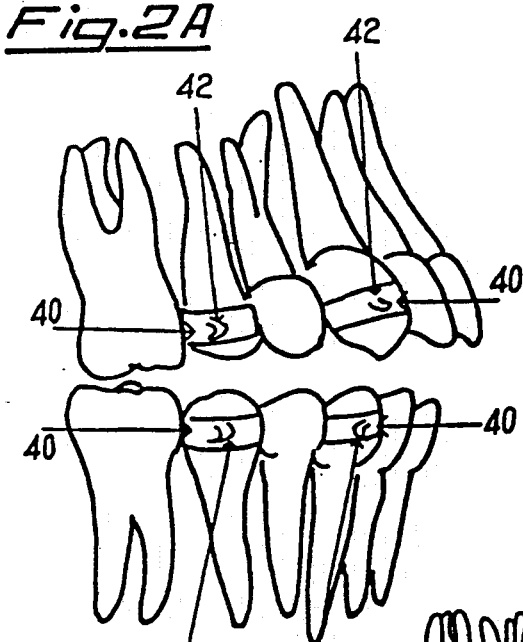
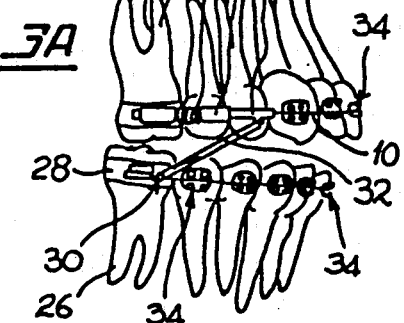
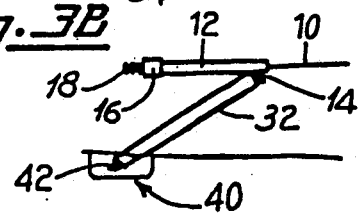
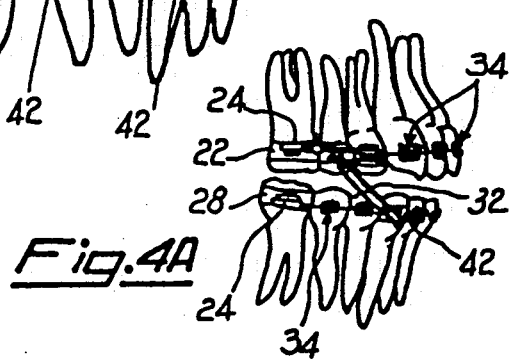
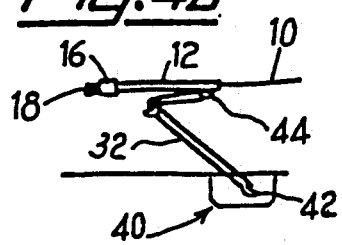

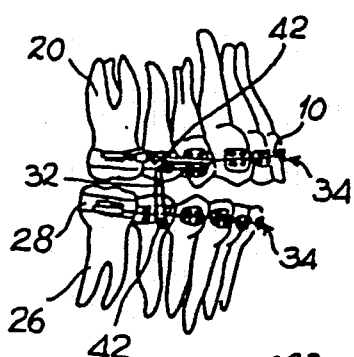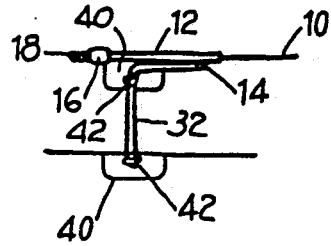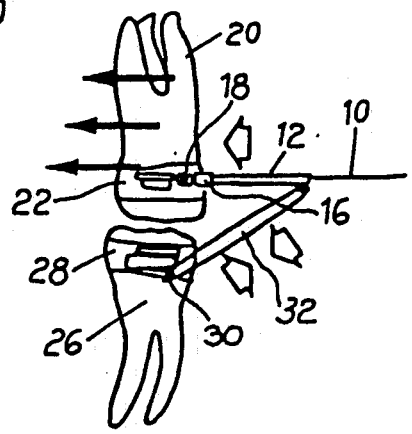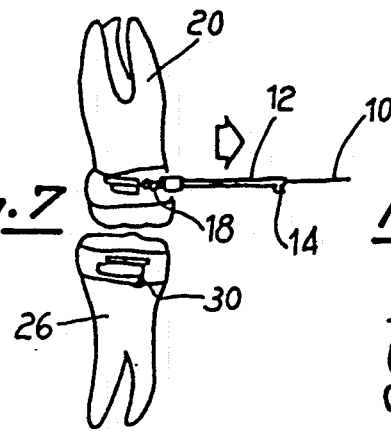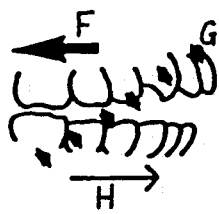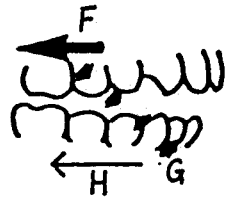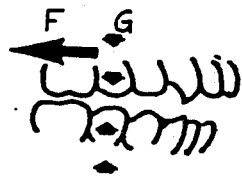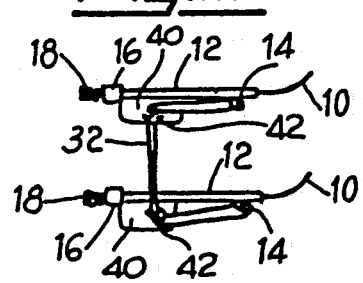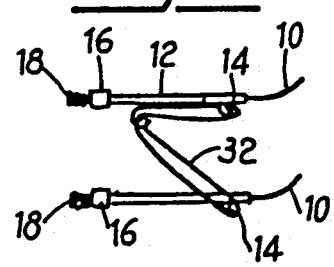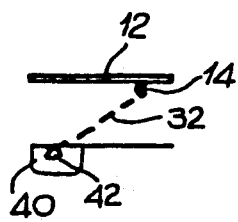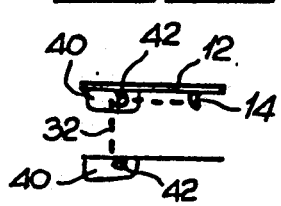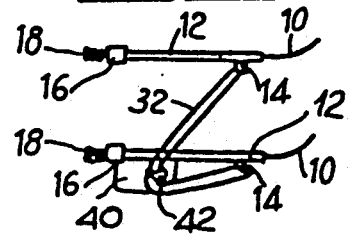

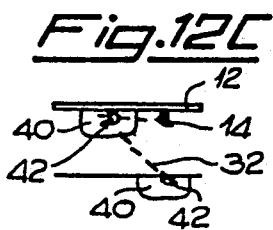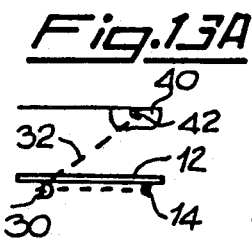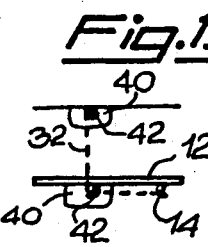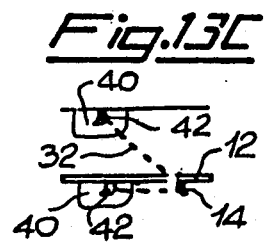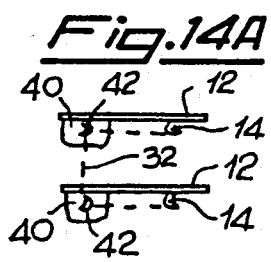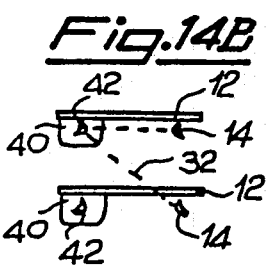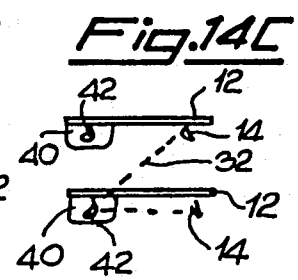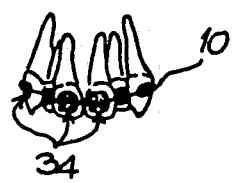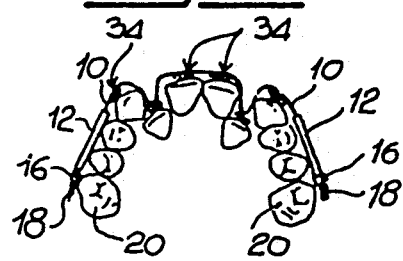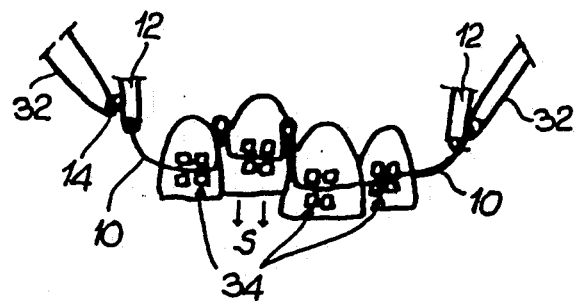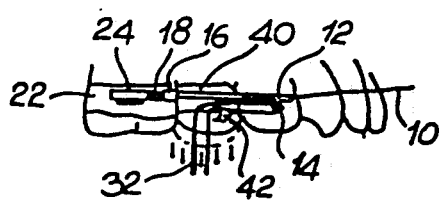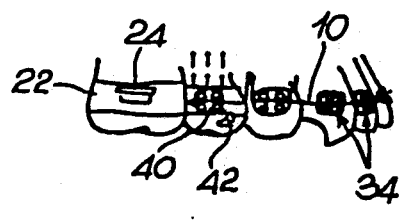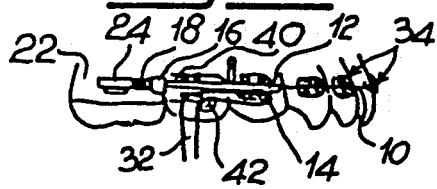

APPLIANCE FOR CORRECTING DENTAL MALPOSITIONS

The present invention relates to an appliance for correcting dental malpositions, and particularly for distalizing molar teeth.

It is known that in orthodontics a number of appliances have been devised for the distalization of molar teeth. These devices can be grouped into two main categories, that is extra-oral and intra-oral appliances.

A particularly effective intra-oral device is the well-known arch invented by Wilson, known as Wilson's Bimetric Arch. The introduction of this orthodontic appliance was a turning-point in the history of orthodontics, since it removed the need for unsightly extra-oral devices, at least in some types of malocclusion, while at the same time greatly reducing treatment time.

However, Wilson's Bimetric Arch has some important disadvantages and limitations, which will be illustrated below. Wilson's device consists of a U-shaped metal arch which is attached to the incisors and to the canines; such metal arch is clamped, at both ends, to two metal tubes, to each of which tubes there is soldered one end of a metal, adjustable loop-shaped stop, while the other end is wound around the tube and free to move along the tube itself in one sense and in the opposite sense. Further along the tube and beyond the adjustable loop, a coil-spring is wound around the tube itself; the coil-spring engages, at one of its ends, the movable part of the loop-shaped stop, and, at the other end, it engages a sleeve fastened onto a metal band which is fitted to a malpositioned molar. By moving the movable end of the loop-shaped stop along the tube, the coil-spring will be compressed and will therefore apply a strong force onto the molar and onto the incisors and canines to which the metal arch is fastened. The molars will be pushed backwards by the acting force, while the incisors and the canines will be pushed forwards by the reaction force. In other words, two groups of teeth (molars on one side, and canines and incisors on the other) will push each other as a result of the compressive force of the coil-spring. Because of the strength exerted by the coil-spring and of the resistance of the stronger molars, this will endanger the stability of the front teeth.

The incisors do not usually require pushing forward, since this would cause their malposition as well as parodontal complications; to prevent this, an inter-maxillary elastic has to be applied to a hook located on the tube of the Bimetric Arch, and to another hook fastened onto the molar of the opposite jaw. In this way, most of the undesired reaction force pressure on the incisors will easily be discharged onto the lower molars, and, in the case of the latter being connected to the other teeth of the lower jaw by means of a non-movable appliance, onto the whole of the inferior dental arch.

Wilson's arch, henceforward shortly referred to as "Bimetric Arch", has the further disadvantage that use of the elastic is obligatory in order to compensate for the reaction forces; this is troublesome to the patient, and since the latter is in most cases a youngster, he/she will tend not to wear the elastic, which would result in very serious mal-position problems with his/her incisors and canines.

The Bimetric Arch has the additional disadvantage of difficulties in anchoring the metal wire to the incisors, when, for example, one or two of the latter are in a backward position. In such cases, prior alignment of the front teeth is imperative, which will lengthen treatment time and will create subsequent anchoring problems, because of the diminished stability of the front teeth as a result of the previous displacement.

Finally, because inter-maxillary elastic traction is of the second class type, use of a Bimetric Arch is unsuitable for upper molar distalization in cases other than II class cases, namely in third canine class cases with upper molar mesialization, and in first dental biprotruded class cases with upper and lower mesialization. The terms "first, second and third class" refer to Angle's classification of malpositions.

An appliance for distalizing molar teeth, which eliminates all of the above-mentioned limitations and disadvantages, has now been devised and is the object of the present invention.

The appliance is of particular advantage since its use will eliminate unwanted vestibularizing force components against the incisors and the canines, and attendant complications; furthermore, this device can be applied not only to second class dental cases, but also to first and third class cases.

The main feature of this appliance, as compared with Wilson's Bimetric Arch, is a different use of the inter-maxillary elastic; the latter is no longer a compensating element, as illustrated above, but rather a fundamental means whereby appropriate displacement of malpositioned teeth is carried out thanks to the exploitation of the muscular force which is exerted in opening the mouth. On the contrary, in the Bimetric Arch, the basic means for moving the teeth is the coil-spring wound around the tube which, when compressed, will apply a force to the teeth. In point of fact, in the appliance according to the invention, the coil-spring is only an element for the transmission of the force of the inter-maxillary elastic, which in turn will transmit the muscular force. In substance it can be said that, wheras with the Bimetric Arch it is the teeth that will push (and tend to move) each other as a result of the expansion force exerted by the spring, in the appliance of the invention it is the muscles that move the teeth through the intermediary of the elastic and the spring.

The characteristics and the advantages of the appliance according to the present invention will become evident from the following detailed description of a non-limiting embodiment, with reference to the attached drawings, in which:

FIG. 1 shows the assembled appliance of the invention;

FIG. 2 illustrates the appliance of the invention (applied to the patient's teeth) for distalizing two upper molars;

FIG. 2A shows the sites of application of the auxiliary bands (with hooks) for premolars and canines;

FIGS. 3A to 5B show three different inter-maxillary elastic tractions;

FIGS. 6 and 7 show the difference between the appliance in operation and at rest;

FIGS. 8 to 10 show the force components of each of the three tractions of the FIGS. 3A to 5B;

FIGS. 11A to 14C schematically show further possible applications of the appliance according to the invention;

FIGS. 15A, 15B and 16 schematically show the use of the appliance in the case of two incisors being in a backward position;

FIGS. 17A, 17B and 17C schematically show additional possible applications of the appliance according to the invention.

FIGS. 1 and 2, to which reference will be made now, show the appliance according to the invention in an embodiment apt to achieve correct positioning of two molars by means of their distalization. Such appliance comprises a metal wire arch (10) and a pair of small metal tubes (12), each housing an end portion of the arm of metal wire (10) which is freely movable inside the tubes; the metal wire is U-shaped because of its intended application to the whole of the dental arch. Each tube (12) is provided, at one end, with a hook projection (14), and, at the other end, with a fixed sleeve (16) against which abuts the end of a coil-spring (18) which is wound around the same tube 12.

FIG. 2 refers to use of the appliance for correcting malposition of two molars, only one of them being represented in the figure. A metal band (22) is fitted onto a malpositioned molar (20). A sleeve (24), housing the freely-moving extremity of tube 12, is attached to band 22. Another band (28) is fitted onto molar 26 (antagonist to molar 20) in a known manner; band 28 is provided with a hook projection (30), and an intermaxillary elastic is engaged on hook 30 and, at the other end, on hook 14 of tube 12. From the above it is clear that, when opening and closing the mouth, the elastic (32) will be tensed, thus applying to tube 12 a force in the direction of molar 20, and this force will be transmitted by spring (18), the spring being compressed between sleeves 16 and 24. It is also evident that this will be the only force generated by the appliance, since tube 12 can move freely around and along wire 10, and therefore the incisors, to which such wire is applied by means of plates 34, will not be subjected to stress. Furthermore it is to be noted that, as the appliance exploits the force the patient has to exert for opening his/her mouth, the amount of force applied to molar 20 can be graded and adjusted through physical exercise applied to the mouth. Moreover, elastics of different sizes and strength can be used, so that the tension of elastic 32 can be made greater, or lesser, or null when the mouth is closed, and this feature, too, will permit adjustment of the force applied to molar 20.

FIGS. 6 and 7 show that, should by any chance the elastic (32) be removed, the coil-spring (18) would be deactivated and tube 12 would slide forward, so that no negative effects would be felt on the incisors.

Application of bands 40 (with hooks 42) to premolar and canine teeth (as in FIG. 2A) will permit modification of the type of inter-maxillary traction.

FIGS. 3A to 5B schematically show three variations of inter-maxillary traction, and more precisely a second-class type traction (FIGS. 3A and 3B), a third-class type traction (FIGS. 4A and 4B), and a vertical type of traction (FIGS. 5A, 5B).

FIGS. 8 to 10 show the force components of each of the three tractions illustrated in FIGS. 3A to 5B, and, in particular, arrows F represent the displacement of the malpositioned molar, arrows G represent the extrusive components, and and arrows H represent the mandibular push.

FIGS. 11A to 11C show that it is possible to apply two devices (one on each jaw) at the same time, thus doubling the performance thereof, whereas the schematic FIGS. 12A to 14C illustrate the possible combinations permitted by the appliance of the invention; more precisely, FIGS. 12A to 12C illustrate distalization of the upper molars in second, first and third class cases respectively; FIGS. 13A to 13C illustrate distalization of the lower molars in second, first and third classes respectively; and FIGS. 14A to 14C illustrate distalization of the upper and lower molars in first, third and second classes respectively.

FIGS. 15A and 15B schematically show how it is possible to use the appliance of the invention also in cases of backward-positioned and overcrowded incisors by appropriately shaping wire 10, and FIG. 16 illustrates how it is possible to obtain additionale auxiliary actions at the same time as the distalization, such as, in the picture, the extrusion of an incisor (arrows S). This is made possible by the fact that the wire can be taken off, and/or substituted, according to necessity, while the rest of the appliance is being kept in operation.

FIGS. 17A to 17C show how it is possible to apply an additional arch on the anterior and bicuspid districts, and to distribute the extrusive push all over the jaw.

From what has been said so far, the advantage of using the appliance according to the invention are evident. It has also been shown that a large number of combinations of the parts is possible, so that the appliance can be defined as modular. Therefore, using the term Arch as in Wilson's Arch, the appliance of the invention can be defined a Modular Arch.

Also, the Modular Arch can be considered an apparatus of a functional kind, since the push on malpositioned teeth is generated through the same force that the patient has to exert in order to open his/her mouth, and therefore such action can be graded by various means (such as thicker and stronger elastics and/or appropriate exercises of mouth movement).

Finally, it is clear that more changes and modifications of the appliance of the invention will be possible without exceeding the fundamental idea and the scope of the same.

I claim:

1. An appliance for correcting dental malpositions, comprising:
    a metal wire arch for application to incisor and canine teeth; at least one metal tube provided, in an intermediate part of said tube with a projection which is engaged by one of the two ends of a coil-spring wound around the tube while the other end engages a sleeve for fastening to a malpositioned tooth, said sleeve receiving a portion of the tube, said tube being provided with at least one hook projection; at said end, said metal wire arch is partially housed and freely movable within the tube, and said hook projection is connected by means of at least one rubber band to a hook projection provided on metal bands for fitting onto one or more teeth.

2. An appliance as claimed in claim 1, wherein said metal wire is separable from the rest of the appliance and therefore replaceable with at least one other metal wire having a different shape and strength to meet the requirements of the treatment to be carried out over the incisors.

3. An appliance as claimed in claim 1, wherein the types of inter-maxillary elastic traction can be changed by further connecting the rubber band to projections provided on metal bands fitted onto premolar or canine teeth.

4. An appliance as claimed in claim 1, wherein removal of the rubber band will annul the force applied to a malpositioned tooth through distension of the coil-spring.

5. An appliance as claimed in claim 1, wherein the projection on the tube comprises a sleeve which is coaxial with and fixed to the former.

6. An appliance as claimed in claim 1, wherein the projection on said tube is made up by an enlarged portion thereof.

7. An appliance for the correction of dental malpositioning comprising:
- a U-shaped archwire for fastening to vestibular surfaces of the canine and incisor teeth of the same dental arch, said archwire encompassing the whole dental arch;
- at least one metal tube provided with a projection in an intermediate part of said tube;
- a sleeve for fastening onto a malpositioned tooth by means of a metal band said sleeve receiving a portion of the tube;
- a coil-spring wound around said tube, having one end abutted against said projection and the other end engaging said sleeve;
- said tube being provided with at least one hook projection;
- wherein said arch wire is partially housed and free to move within the tube;
- and wherein said hook projection is connected by means of at least one rubber band to a hook projection fastened on at least one metal band which is fitted onto one or more teeth.

8. An appliance as claimed in claim 7, wherein said metal wire is separable from the rest of the device, and therefore replaceable with at least one other metal wire having a different shape and strength to meet the requirements of the treatment to be carried out over the incisors.

9. An appliance as claimed in claim 7, wherein the types of inter-maxillary elastic traction can be changed by further connecting the rubber band to projections provided on metal bands which are fitted onto premolar or canine teeth.

10. An appliance as claimed in claim 7, wherein removal of the rubber band will annul the force applied to a malpositioned tooth through distension of the coil-spring.

11. An appliance as claimed in claim 7, wherein the projection on the tube comprises a sleeve which is coaxial with and fixed to the former.

12. An appliance as claimed in claim 7, wherein the projection on said tube is made up by an enlarged portion thereof.

13. An appliance for correcting dental malpositions comprising:
- a metal wire arch for fastening to the vestibular surface of the front teeth;
- a least one metal tube surrounding said metal wire;
- a sleeve fastened to a malpositioned tooth;
- said metal tube having a hook at one end;
- said metal tube having means to abut a spring at the other end;
- a spring compressed between said sleeve and said means to abut a spring on said tube; and
- means within said coil-spring for retaining said spring in place between said tube and said means to abut.

14. The appliance in accordance with claim 13 wherein said means within said spring is an extension of said tube which passes inside of said spring and into said sleeve.

15. The appliance in accordance with claim 13 wherein said front teeth are canine and incisor teeth.

16. The appliance in accordance with claim 13 wherein said coil spring moves said metal tube as the jaw is moved, whereby the position of said hook is moved with respect to the pivot point of the patients jaw.

* * * * *